United States Patent [19]

Klein

[11] Patent Number: 5,002,889

[45] Date of Patent: Mar. 26, 1991

[54] REACTION WELL SHAPE FOR A MICROWELL TRAY

[75] Inventor: Gerald L. Klein, Edmonds, Wash.

[73] Assignee: Genetic Systems Corporation, Redmond, Wash.

[21] Appl. No.: 260,836

[22] Filed: Oct. 21, 1988

[51] Int. Cl.[5] .................... C12M 3/00

[52] U.S. Cl. .................... 435/284; 435/287; 422/102

[58] Field of Search .................... 435/296, 287, 284, 293, 435/301; 215/1 R; D7/6; 422/102

[56] References Cited

U.S. PATENT DOCUMENTS

| | | | |
|---|---|---|---|
| D. 282,997 | 3/1986 | Miller | D7/6 |
| 3,140,007 | 7/1964 | Nettleship | 215/10 |
| 3,508,183 | 4/1970 | Pinckard | 215/1 R |
| 4,154,795 | 5/1979 | Thorne . | |
| 4,246,339 | 1/1981 | Cole et al. . | |
| 4,263,256 | 4/1981 | Morle . | |
| 4,292,273 | 9/1981 | Butz et al. | 435/301 |
| 4,468,371 | 8/1984 | Chen et al. . | |
| 4,545,958 | 10/1985 | Dopatka . | |
| 4,599,315 | 7/1986 | Terasaki et al. . | |
| 4,657,867 | 4/1987 | Guhl et al. . | |

*Primary Examiner*—Carroll B. Dority
*Attorney, Agent, or Firm*—Townsend and Towsend

[57] ABSTRACT

A microwell for enzyme-linked immunosorbent assays has a concavely curved, circumferential sidewall, a flat optical bottom and a top lip, including smooth transitions between the top lip, concave sidewall and flat bottom. This shape minimizes the tendency of fluid to cling to the well for washing efficiency and maximizes a vertical optical path length of fluid in the well for improved optical determination.

16 Claims, 1 Drawing Sheet

REACTION WELL SHAPE FOR A MICROWELL TRAY

DESCRIPTION

1. Technical Field

The invention relates to well shapes for chemical reactions. More specifically, the invention relates to well shapes for reacting small biological sample volumes.

2. Background Art

In the field of biotechnology, there is an increasing use of Enzyme Linked Immunosorbent Assays (ELISA) for the detection of selected analytes, such as antigens or antibodies. Research towards improving the specificity and sensitivity of this assay procedure is providing methods for detecting analytes of interest at diminishingly lower concentrations and fluid sample volumes. Trays containing a plurality of reaction wells, also known as "microwells", have become well known in the art by the generic designation "terasaki" plates after a well-known researcher in the field of ELISA methods. Such plates typically comprise a matrix array of wells spaced at regular intervals in rows and columns. A plurality of wells are provided on each plate so that different patient samples can be simultaneously reacted with reactants.

ELISA techniques have been developed for the detection of a variety of analytes, including the hepatitis B surface antigen and the acquired immune deficiency syndrome antibody. In a conventional hepatitis B antigen determination, a microwell is coated with an immune reactant antibody for the hepatitis B antigen. A solution containing patient sample (such as blood) is introduced into the well. As the antigens are free to move through the solution by diffusion, each molecule of the antigen will bind to the antibody coating on the well if a satisfactory incubation time and temperature for the well are selected. Preferably, sufficient antibody is coated on the well sidewall to remove all of the hepatitis B antigen from the solution. In a subsequent step, the remaining solution, containing other nonspecific molecules, is removed from the well and the well sidewall washed to free all of the unbound nonspecific molecules. A second solution, containing antibodies to which an enzyme has been chemically tied (conjugated), is then placed in the well and exposed to the coated sidewall. The conjugated antibody is chosen to recognize a secondary immunological characteristic of the hepatitis B antigen, which is now bound to the antibody coating on the well sidewall. This conjugate will ideally be present in a concentration considerably in excess to the expected concentration range of the hepatitis B antibody. This coated well and solution are then incubated so that the conjugated antibody will bind to every hepatitis B antigen previously linked to the hepatitis B antibody which has been linked to the coated well sidewall. At the end of the incubation period, the solution containing the unbound excess conjugate must be removed from the well and the surface again washed. Finally, a third solution is added containing a compound which reacts with the enzyme to produce a measurable response, such as a proportional color change. Photometry or other measurement techniques can be used to determine the quality and quantity of hepatitis B antigen present in the wells, and thus in the original patient sample.

Washing unbound antibodies, enzymes, etc., from the wells is extremely important in providing quantitative measurements with low signal-to-noise ratio. The present trend toward miniaturizing reaction wells to reduce the cost of preparing coated terasaki plates aggravates the washing problem. As smaller well volumes are approached, the physical properties of liquid-solid interactions (surface tension, capillary action, etc.), exert a greater effect on the behavior of the solution. Small containment volumes can firmly retain a liquid. As the containment volumes decrease, meniscus effects become more exaggerated and surface tension can cause air to be stubbornly entrapped below a liquid. The demands of washing efficiency therefore favor a shallow open form to minimize solution entrapment. However, this design criterion is contrary to photometric requirements, which favor a narrow, constricted shape for maximizing an optical path length through the solution.

Therefore, a need exists for a microwell shape which is easily washed and does not tend to retain fluid and which also provides a long, effective, vertical path length for photometric measurements of a characteristic of the fluid.

SUMMARY OF THE INVENTION

It is an object of the present invention to provide a microwell shape which washes easily and which does not tend to retain fluid in the well.

It is also an object of the present invention to achieve the above object while providing a well shape having a small volume and a relatively long, vertical path length for photometric determinations.

It is another object of the present invention to achieve the above two objects with a well shape which is relatively easy and inexpensive to manufacture.

The invention achieves these and other objects and advantages, which will become apparent from the description which follows, by providing a well having a circumferential, concave sidewall, a circumferential top that defines an opening for the well, and a bottom for the well, with smooth transitions between the concavely curved sidewall and top lip and well bottom, respectively.

In the preferred embodiment, the reaction well has a convex, circumferential top lip centered about a vertical well axis. A concave, circumferential sidewall is contiguous with the top lip. A circular, optical window is centered about the well axis and forms a bottom for the well. A concave, circumferential transition wall connects the sidewall with the optical window. This structure optimizes washing efficiency and provides a maximum vertical path length along the well axis for optical photometry. The circumferential top lip and circumferential transition walls are provided with a radius of curvature which is substantially smaller than the radius of curvature for the circumferential sidewall. The sidewall may have a parabolic curvature, or may approximate a parabola with a constant radius of curvature for a spherical shape.

BEST MODE FOR CARRYING OUT THE INVENTION

Figure 2:
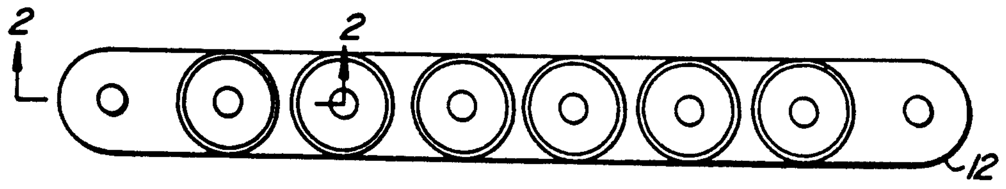
FIG. 2 is a top plan view of a strip of microwells.
Figure 1:
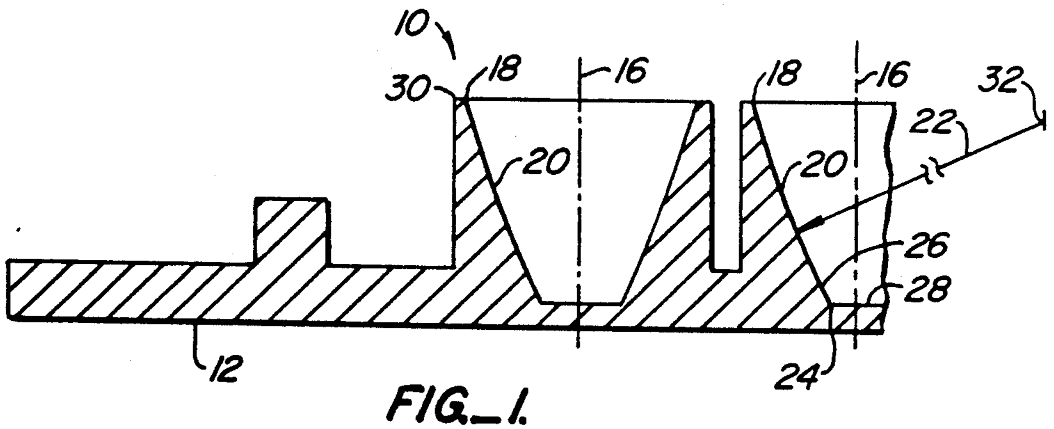
FIG. 1 is an enlarged, sectional, elevational view of a microwell shape of the present invention.
Figure 3:
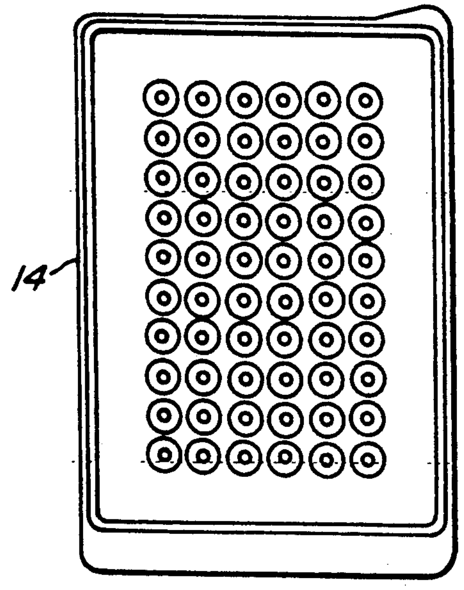
FIG. 3 is a top plan view of a microwell tray employing a plurality of the strips shown in FIG. 2.

A microwell, in accordance with the present invention, is generally indicated at reference numeral 10 in FIG. 1. Six wells are combined in a row so as to form a strip 12, as shown in FIG. 2. A plurality of strips 12 may be selectively combined in a microwell plate 14, shown in FIG. 3 for use in an ELISA determination. Although the well of the present invention is shown used in a microwell plate 14, those of ordinary skill in the art will readily recognize that the geometric relationships described below may be employed with single well designs or multiple well designs other than those shown in FIGS. 2 and 3.

As shown in FIG. 1, the microwell 10 has four circumferential sections concentrically aligned with respect to a vertical well axis 16. The geometric relationships of the circumferential sections are intended to avoid the sharp corners and transitions of prior well designs, thereby facilitating the expulsion or removal of solutions contained therein. The first of the four sections is a convex top lip 18 which has a radius of curvature of approximately 0.012 inch with respect to a horizontal, circular axis external to the well 10. A second section comprises a concave, circumferential sidewall 20 having a radius of curvature 22 of approximately 0.380 inch. Sidewall 20 is contiguous or tangential with the top lip 18 such that tangents to the respective sections at a junction therebetween are parallel and congruent.

A third one of the sections comprises a circumferential transition wall 24. The transition wall is contiguous with a lower edge 26 of the circumferential sidewall 20 and joins the circumferential sidewall with a circular, planar, optical window 28 which forms a bottom for the well 10. The optical window 28 is the fourth section. The transition wall 24 has a radius of curvature of approximately 0.012 inch, as does the convex top lip 18. The transition wall must be tangent to both the sidewall and the planar optical window.

The well 10 has an open top defined by an upper edge 30 of the circumferential top lip 18. The open top has a diameter of approximately 0.220 inch. The optical window has a diameter of approximately 0.059 inch. The well has a depth measured from the open top to the optical window 28, measured along the vertical well axis 16, of approximately 0.20 inch. It has been found that these dimensions, in conjunction with the curvatures described above, provide an optimal well shape which minimizes the tendency of fluid to adhere to the well, which maximizes the optical path length of the fluid for photometric determinations, and which minimizes the volume of the well.

The curvature of the concave, circumferential sidewall 20 preferably approximates the shape of a parabola. However, it has been found that a concave, circumferential sidewall 20, which has a surface of revolution having the 0.380 curvature radius described above, closely approximates the desired parabolic shape while being substantially less expensive to manufacture. The preferred radius of curvature of 0,380 inch for the above-described well is measured with respect to a horizontal, circular axis 32, displaced approximately 0.223 inch above the optical window 28 and centered about the vertical well axis 16, and having a diameter of approximately 0.556 inch.

The geometry described above differs substantially from the geometry of prior art microwells. The majority of microwells presently available have sidewalls with substantially constant slopes between an upper rim and a flat bottom surface. The sidewall 20 of the present invention has a constantly changing slope when viewed in cross section, as shown in FIG. 1. Some microwell designs, such as the design disclosed in U.S. Pat. No. 4,599,315, issued to Terasaki et al., disclose curved well sidewalls which are convexly curved, as opposed to the concavely curved sidewall of the present invention.

In view of the above, variations consistent with the above description are contemplated. Therefore, the invention is not to be limited by the above description but is to be determined in scope by the claims which follow.

I claim:

1. An apparatus comprising a molded device having a plurality of reaction wells adapted for photometric determination of a fluid characteristic, each reaction well having a volume capacity of less than one milliliter and comprising;

a convexly curved, circumferential top lip centered about a vertical well axis and defining an opening for the well;

a concavely curved, circumferential sidewall centered about the well axis and contiguous with the top lip and having a radiums of curvature of approximately 0.38 inch as measured about the vertical well axis approximately 0.223 inches above a well bottom;

a concavely curved, circumferential transition wall centered about the well axis and contiguous with the circumferential sidewall; and a circular, planar optical window centered about the well axis and contiguous with the transition wall so as to define the bottom for the well, wherein the circumferential top lip and circumferential transition wall have radii of curvature substantially less than the radius of curvature of the circumferential sidewall.

2. The reaction well of claim 1 wherein the circumferential sidewall has a parabolic shape.

3. The reaction well of claim 1 wherein the circumferential sidewall is a surface of revolution.

4. The reaction well of claim 1 wherein the circumferential top lip and circumferential transition wall have a radius of curvature of approximately 0.012 inch.

5. The reaction well of claim 4 wherein the circumferential top lip has a diameter of approximately 0.22 inch.

6. The reaction well of claim 5 wherein the optical window has a diameter of approximately 0.059 inch.

7. The reaction well of claim 6 wherein the well has a height, defined by a distance between the circumferential top lip and the optical window, of approximately 0.180 inch measured along the well axis.

8. The reaction well of claim 1 wherein the circumferential top lip and circumferential sidewall have tangents, at respective contiguous portions thereof, which are parallel.

9. The reaction well of claim 1 wherein the circumferential sidewall and circumferential transition wall have tangents, at respective contiguous portions thereof, which are parallel.

10. The well shape of claim 1 wherein the circumferential sidewalls, and the circumferential top lip and transition wall, have tangents, at respective contiguous portions thereof, which are parallel.

11. An apparatus comprising a molded device having a plurality of reaction wells for photometric determination of a fluid characteristic, each well having a volume capacity of less than one milliliter and the shape of the well comprising;

a circumferential top lip defining an open top for the well;

a peripheral, substantially concavely curved sidewall contiguous with the top lip and having a smooth transition therebetween and having a radius of curvature of approximately 0.38 inch as measured above a well bottom; and axis approximately 0.223 inches above a well bottom; and a substantially flat optical window connected to the curved sidewall and having a smooth transition there between defining the bottom for the well.

12. The well shape of claim 11 wherein the curved sidewall has a parabolic curve.

13. The well shape of claim 11 wherein the curved a sidewall has a spherical curve.

14. The apparatus of claim 1, wherein the reaction wells are combined in a row to form a strip.

15. The apparatus of claim 11, wherein the reaction wells are combined in a row to form a strip.

16. The apparatus of claim 11, wherein the wells are formed in a place.

* * * * *